(12) United States Patent
Ristol Debart et al.

(10) Patent No.: US 7,442,308 B2
(45) Date of Patent: Oct. 28, 2008

(54) PROCESS FOR REMOVING VIRUSES IN FIBRINOGEN SOLUTIONS AND FIBRINOGEN OBTAINED BY SAID PROCESS

(75) Inventors: Pere Ristol Debart, Sabadell (ES); Jesus Fernandez Rodriguez, Gava (ES)

(73) Assignee: Grifols, S.A., Barcelona (ES)

( * ) Notice: Subject to any disclaimer, the term of this patent is extended or adjusted under 35 U.S.C. 154(b) by 142 days.

(21) Appl. No.: 10/788,049

(22) Filed: Feb. 25, 2004

(65) Prior Publication Data

US 2004/0173527 A1 Sep. 9, 2004

(30) Foreign Application Priority Data

Mar. 6, 2003 (ES) ................................ 200300538

(51) Int. Cl.
*B01D 61/58* (2006.01)
*B01D 61/14* (2006.01)
*A61K 35/16* (2006.01)
*B01D 61/00* (2006.01)
*A61K 35/00* (2006.01)

(52) U.S. Cl. .................. 210/651; 210/634; 210/771; 514/21; 530/382; 530/412; 530/414; 530/418; 530/421; 435/2; 424/530

(58) Field of Classification Search ................ None
See application file for complete search history.

(56) References Cited

U.S. PATENT DOCUMENTS

| 4,141,887 | A | | 2/1979 | Seufert | |
|---|---|---|---|---|---|
| 5,506,127 | A | | 4/1996 | Proba | |
| 5,605,887 | A | * | 2/1997 | Pines et al. | 514/21 |
| 5,981,254 | A | | 11/1999 | Bui-Khac | |
| 6,270,672 | B1 | * | 8/2001 | Turecek et al. | 210/645 |
| 6,468,733 | B2 | * | 10/2002 | Nur et al. | 435/2 |
| 6,967,239 | B1 | * | 11/2005 | Chtourou et al. | 530/383 |
| 2001/0051154 | A1 | | 12/2001 | Roemisch et al. | |
| 2003/0232969 | A1 | * | 12/2003 | Lengsfeld et al. | 530/383 |

FOREIGN PATENT DOCUMENTS

| EP | 1 161 958 A1 | 12/2001 |
|---|---|---|
| EP | 1 250 929 | 10/2002 |
| ES | 2 156 731 | 1/2001 |
| JP | 07-173073 | 7/1995 |
| JP | 2001 335509 | 12/2001 |
| WO | WO 98/37086 | 8/1998 |
| WO | WO 99/23111 | 5/1999 |

OTHER PUBLICATIONS

Peter L Roberts, "Valus of virus filtration as a method of improving the safety of plasma products", Vox Sang 1995; 69; 82-83.*
Gilbert, et al ("Purification of fibrinogen and virus removal using preparative electrophoresis", Annals of the New York Academy of Sciences 936: 625-629 (2001)).*
Cohn, et al., J. Am. Chem. Soc. (1946) 68:459-475.
Burnouf, Blood Reviews (2000) 14:94-110.
Morgenthaler, Vox Sang (2000) 78 (Supp. 2):217-221.
Jackson, Am. J. of Surgery (2001) 182:1S-7S.
Martinowitz, et al., U.Curr. Opin. Hematol (1996) 3:395-402
T. Burnouf et al., "Nanofiltration of plasma-derived biopharmaceutical products", *Haemophilia* 9:24-37, XP-001181709 (Jan. 2003).

* cited by examiner

*Primary Examiner*—Krishnan S Menon
(74) *Attorney, Agent, or Firm*—Darby & Darby, P.C.

(57) ABSTRACT

A process for removing viruses in fibrinogen solutions and fibrinogen obtained thereof wherein the process starts with an adjusted purified fibrinogen solution, the adjusted purified solution is frozen and then thawed at a temperature between 5 and 20° C., the undissolved materials associated with the fibrinogen are subsequently separated, the temperature is adjusted and the resultant solution is finally subjected to nanofiltration using filters having a pore size smaller than 35 nm.

16 Claims, No Drawings

PROCESS FOR REMOVING VIRUSES IN FIBRINOGEN SOLUTIONS AND FIBRINOGEN OBTAINED BY SAID PROCESS

The present invention relates to a process for removing viruses in fibrinogen solutions by nanofiltration and also relates to fibrinogen for therapeutic application obtained by the said process.

PRIOR ART

Plasma fibrinogen, a glycoprotein having a molecular weight of 340,000 daltons, is the coagulation factor activated at the end of the coagulation cascade during hemostasis. This fibrinogen is involved in primary hemostasis, during platelet aggregation, and secondary hemostasis, during the formation of the fibrin clot.

Fibrinogen as a therapeutic product, which is a protein purified from the human plasma, is used for substitutive therapy in situations where there is a deficit of this protein and, as a component of fibrin adhesives, in hemostasis and the sealing of wounds, in tissue reconstruction, as a biological glue and as a vehicle for the liberation of medicines and hormones, among other applications.

For commercial use, fibrinogen is prepared from human plasma from numerous donors ("a pool"). Despite the controls carried out on the donors and donations at the blood banks, plasma units, mini pools and industrial pools for fractionation, the possibility of contamination by haematic viruses cannot be ruled out. Therefore, specific virus eliminating stages are introduced into the plasma protein purification processes. This is of great importance for this protein which can be purified on an industrial scale starting from cryoprecipitate or from FrI (first fraction) using the Cohn method [Cohn J. et al.; J Am Chem Soc (1946) 68, 459-475] since potentially a larger content of viruses is entrained since the starting material is located at the beginning of the fractionation of the plasma and, furthermore, it does not have the reducing effect of the subsequent fractionation with ethanol.

From the methods of reducing the viral content, used in plasma protein purification processes, the following should be emphasised as they are widely used and have a proven efficiency:
  heat treatments. These have the potential to reduce the effective viral content with respect both to enveloped viruses and to unenveloped viruses. Its efficiency is directly related to the thermal stability of the protein and to the added stabiliser. Therefore, they have the drawback that the protein molecule is subject to variations which lead to the formation of neoantigenicity [CPMP/ Note for guidance on plasma derived products (CPMP/ BWP/269/95rev. 3) January 2001].
  treatments with organic solvents (OSD). Owing to their high efficiency in the inactivation of viruses having a lipid envelope, this is a widely used treatment which can be considered as a reference for viruses of these types. On the other hand, it has no effect on viruses without a lipid envelope such as the Parvovirus and Hepatitis A virus [Burnouf T. Blood Reviews (2000) 14, 94-110; Martinowitz U. Curr. Opin. Hematol (1996) 3, 395-402].
On the other hand, there is a tendency nowadays to include at least two complementary stages of virus removal.
  the filtration of solutions through filters having a pore size capable of retaining viral particles is a method which has been more widely used in recent years. It is a physical process which, in principle, is not capable of affecting the structure of the proteins and has an efficient capability of removing the viral content, depending on the pore size used. This pore size is particularly conditional on the spatial dimension of the protein molecule to be filtered (which has to pass through the filter). Filtration through filters of 20 nm or less may guarantee a significant reduction in the unenveloped viruses of small size such as the Hepatitis A virus and the Parvovirus which are between 20 and 30 nm. On the other hand, filtration through filters having a greater pore size (35 nm or greater) will not guarantee a sufficient level of safety against these viruses. The difficulty of this method obviously appears unsolvable when the size differences between virus and protein tend to disappear [J. J. Morgenthaler, Vox Sang (2000) 78 (suppl 2), 217-221].

Industrial application of fibrinogen solution nanofiltration through 35 nm filters has been described but not through filters having a smaller pore size. Owing to its characteristics of molecular size and stability, fibrinogen is a protein which poses filtration problems, even when sterilisation by filtration through filters having a pore size of 0.2 μm is attempted.

PCT patent application WO 99/23111 describes and claims the filtration of a fibrinogen solution through a filter having a pore size of 35 nm by addition of a detergent which allows said filtration while avoiding a substantial loss of protein which would make this industrial application unviable.

PCT patent application WO 98/37086 finds that the presence of proteins having a high molecular weight (higher than 150 kD), which include fibrinogen, complicates the filtration of smaller proteins through 15 nm nanofilters. This patent application describes a method of removing such high molecular weight proteins (including fibrinogen) with the aim of allowing nanofiltration. Therefore, this is not the object of the present invention, but demonstrates the problem of nanofiltration of high molecular weight molecules.

European patent EP 1 161 958 A1 describes a method for inactivating viruses in biological liquids. In the described process, the pore size of the nanofilter is dependent on the size of the protein to be filtered, the examples showing filtration through 35 nm and involving the prior chromatography of the solution to be filtered with the object of facilitating said nanofiltration. This patent demonstrates the difficulty in carrying out nanofiltration, even through 35 nm, when the protein is of a considerable size.

Patent application US 2001/0051154 A1 describes the stabilization of proteins, including fibrinogen, with the aim of protecting them from the loss of activity or denaturation during the treatment to reduce the viral content both by pasteurization and by nanofiltration. This process involves the addition of a large quantity of sugars (0.5 g/ml) and one or more amino acids (>0.5 mol/l). However, this patent application neither describes nor provides examples of the nanofiltration of fibrinogen, so it cannot be deduced that the nanofiltration of fibrinogen can be carried out through filters having a pore size smaller than 35 nm.

Fibrinogen preparations, as a component of fibrin adhesives, which are commercially available nowadays [M. R. Jackson, The American Journal of Surgery (2001) 182, 1S-7S], employ methods of reducing the viral content which basically consist of thermal treatments and treatments with OSD. Nanofiltration does not appear to be a method of choice, probably on account of the fact that filtration through 35 nm (or a greater pore size) is not effective for small viruses which have not been removed by OSD or the heat treatment.

SUMMARY OF THE INVENTION

The present invention allows the filtration of a fibrinogen solution through filters having a nominal pore size smaller than 35 nm under conditions of processing time, filtration area and protein recovery which allow the industrial application thereof in the production of purified fibrinogen as a therapeutic product. This filtration is achieved through the prior freezing and thawing of the purified fibrinogen solution under controlled conditions. The inventors have surprisingly found that, with this controlled freezing and thawing, insoluble, aggregated or partially denatured material is precipitated that would, in practice, prevent the filtration of the solution through pore sizes smaller than 35 nm. Separation of the precipitated material allows nanofiltration to a pore size smaller than 35 nm.

DETAILED DESCRIPTION OF THE INVENTION

The cryoprecipitate, the first fraction (FrI) of the Cohn method or an equivalent fibrinogen-containing fraction may be used as the starting material for the purification of fibrinogen originating from human plasma from which a purified fibrinogen precipitate is obtained by precipitation, preferably with glycine.

The starting fraction, prior to dissolution and clarification, may be subjected to a treatment with an organic solvent and detergent (OSD) with the object of inactivating the possible viruses with a lipid envelope that may be present. The OSD may be removed by any known method such as chromatography or, preferably in this case, by precipitation with glycine.

The fibrinogen-rich purified fraction may be dissolved, clarified by filtration or centrifugation and adjusted with stabilizers, preferably amino acids (e.g., arginine, glycine or equivalent) and carbohydrates (e.g., saccharose), with a pH preferably between 6.0 and 8.0 and an ion content preferably adjusted by sodium chloride at physiologically acceptable concentrations.

Starting from the aforementioned adjusted and purified fibrinogen solution with purity preferably higher than or equal to 80%, the inventors have surprisingly found that, by freezing and thawing the solution at a controlled temperature between 5 and 20° C., and preferably between 8 and 13° C., the readily aggregated or denatured unstable components associated with the fibrinogen are insolubilised. These materials may easily be separated by clarification through a nylon, metal mesh or preferably by decanting, centrifuging or direct filtration, preferably with a gradient of filters, or by combination of any of the aforementioned methods. The resulting material can surprisingly be subjected to nanofiltration even through pores smaller than 35 nm, with very acceptable productivity and recovery.

A preferred method of carrying out the present invention will be described hereinafter. The material resulting from this clarification, diluted to a concentration lower than or equal to 1.5 mg/ml in the presence of at least one amino acid (preferably arginine) at a concentration between 0.1 and 8% (weight/volume) and a temperature between 18 and 37° C., preferably in both cases, and previously clarified through filters having a greater pore size, is filtered through a nanofilter having a pore size smaller than 35 nm (preferably about 20 nm), with protein recovery greater than 80%. The filter area required to carry out this nanofiltration is between 10 and 1,000 cm$^2$ per litre of solution to be filtered, depending on the protein concentration of the solution and the pore size of the nanofilter used. The processing time is usually shorter than 12 hours.

The data obtained for protein recovery, necessary filter area and processing time required, together with the characterisation of the product obtained, show the applicability of the invention in an industrialisable process.

PRACTICAL EXAMPLES OF THE INVENTION

Example 1

Fraction I precipitated with 8% cold ethanol according to Cohn's method was used as the starting material. 10 kg of said fraction I was suspended at a ratio of 1:9 with a buffer solution containing sodium citrate-chloride, as well as an anticoagulant and an antifibrinolytic. The suspension was clarified at 30° C. through depth filters made of polypropylene and cellulose esters (both from Millipore) to a particle size of approximately 0.5 microns.

The solution was then submitted to a viral inactivation treatment with solvent/detergent, using 0.3% tri-n-butyl phosphate and 1% polysorbate 80, and incubating at 27° C. for no less than 6 hours. The inactivated solution was cooled at 9° C. and was precipitated by addition of glycine to a concentration of 1.7 M. The precipitate formed was separated by centrifugation at approximately 15,000 rpm using a Sharples centrifuge having a capacity of 5 kg, and was then suspended in a sodium chloride-citrate solution, and was precipitated again with glycine to 1.5 M. The precipitate formed was again separated by centrifugation and was then reprecipitated in the same way as in the previous stage.

The resulting precipitate (3$^{rd}$ glycine precipitate) accounts for 60-80% of the starting fraction I weight and consists of approximately 15% of dry protein, approximately 90% being fibrinogen. This material (was) dissolved at 30° C. with a ratio of 1:3 of a 3.4% saccharose solution and an isotonic concentration of sodium chloride-citrate salts, and was subsequently filtered through depth and clarifying filters (both from Millipore) to a pore size of 1 μm. Approximately 30 litres of the solution were obtained.

The material was diafiltered through 100 kDa membranes (from Pall-Filtron) against 1% arginine to remove the excess salts, saccharose and glycine, and once it had reached a fibrinogen content of 1.5%, formulated with 0.5% albumin, it was clarified through 0.5 microns and sterilely filtered through 0.2 microns.

Starting with the aforementioned sterile solution, an attempt was made to filter through 0.1 microns through 47 mm diameter discs (Pall DVD and DJL) but the filter got blocked almost immediately (in approximately 5 to 10 minutes) and less than about 5 ml of the solution was filtered, a reduction of 2.1 AU of OD (from 27.2 AU to 25.1 AU) being observed in the filtrate. These results were unsatisfactory and demonstrated the problems with fibrinogen filtration, even through filters having a pore size of 0.1 microns.

The solution filtered through 0.2 microns was frozen at −70° C. to perform subsequent filtration tests.

Example 2

The solution filtered through 0.2 microns in example 1 was completely thawed at 30° C. in order to carry out nanofiltration tests at various fibrinogen concentrations, the possible positive effect on filterability being investigated by carrying out extreme dilution, as a process for dispersing the fibrinogen molecules in the presence of an amino acid solution (arginine).

An aliquot portion of the solution filtered through 0.2 microns was subjected to various dilutions with 0.66% arginine solution, 2.7 mM sodium citrate and 62.6 mM sodium chloride at pH 7.0 and 30° C. so that the final fibrinogen concentrations were approximately 5, 3, 1, 0.7 and 0.5 mg/ml.

Each diluted solution was filtered through 0.1 microns, just prior to carrying out nanofiltration through a cartridge having a pore size of 35 nm (BMM-Planova 35N from Asahi-Kasei) and an area of 10 cm². The pressure conditions were as recommended by the manufacturer: 0.2 to 1.0 bar; and the temperature was 25 to 30° C. during all the filtration processes.

The filterability and recovery results obtained are shown in Table 1.

Table 1

TABLE 1

| Fibrinogen (mg/ml) | Filtered protein (g/m²) | Recovery (%) |
|---|---|---|
| 5 | 19 | 20 |
| 3 | 30 | 35 |
| 1 | 46/50 | 61/56 |
| 0.7 | 50 | 62 |
| 0.5 | 65 | 69 |

It can be deduced from the foregoing values that nanofiltration through 35 nm can be carried out only if the fibrinogen concentration is very diluted, preferably to between 1 and 0.5 mg/ml or lower, acceptable values for filtration capacity (g of fibrinogen/m²) and recovery (>50% of fibrinogen) being achieved within this range.

Obviously, one of the main drawbacks of nanofiltration in very dilute conditions resides in the excessive volume to be filtered and in the subsequent final concentration of the product prior to dosing, which is why the optimum would be at the upper value of the established range.

Even under the best processing conditions, it is obvious that it is difficult to subject the product to nanofiltration through 35 nm by proceeding in the above-described manner which involves thawing the product and completely dissolving the fibrinogen at 30° C.

Example 3

A further batch was processed in the manner described in example 1 until the solubilised and clarified glycine precipitate III was obtained, a portion of which was frozen at −70° C. for the preservation thereof. The remainder of the solution was processed in the manner described in example 1 to the final product filtered through 0.2 microns.

A comparative nanofiltration test was carried out through 20 nm (Pall's Ultipor-DV20) with 47 mm diameter discs, using fresh material (final product filtered through 0.2 microns without freezing) and the corresponding frozen material, both with a fibrinogen concentration of 0.73 to 0.74 mg/ml, the pressure applied being that recommended by the filter manufacturer (Pall) of 2.2 to 2.8 bar.

In the case of the frozen material, total thawing was first carried out at ambient temperature (temperature of the solution <20° C.) and the material was clarified through 0.5 microns. Both the fresh material and the frozen material were conveniently diluted with 2% arginine solution (w/v), 62.6 mM sodium chloride and 2.7 mM sodium citrate, pH 7.0 and 30° C., and were filtered through 0.1 microns just prior to staged nanofiltration through 50 nm (DV50) and 20 nm (DV20) at a temperature of approximately 30° C.

The results of the two processes are summarised in Table 2.

TABLE 2

| | Volume filtered (1) through DV20 | Filtered protein (g/m²) | Recovery % | Filtration time (h) |
|---|---|---|---|---|
| Fresh material | 29.0 (*) | 23.7 | 99.4 | 5.00 |
| Frozen material | 37.0 | 30.1 | 99.7 | 1.42 |

* The filter became blocked at the aforementioned volume, so nanofiltration could not be completed.

The test with fresh material (without freezing) yielded protein recovery of 99.4%, but the maximum amount which could be filtered before the DV20 filter became blocked was only 23.7 g of fibrinogen/m², and the average flow rate of fibrinogen was 4.74 g/m²/hour (23.7 divided by 5.00).

With the frozen material, on the other hand, the recovery was 99.7% of protein and the DV20 filter did not become blocked when a fibrinogen load of 30.1 g/m² was applied, the average fibrinogen flow rate being 21.20 g/m²/hour. It could be seen clearly that the nanofiltration of more than 30.1 g of protein is possible with the controlled stage of freezing and thawing since there was no abnormal reduction in the filtrate flow rate in this test, indicating the absence of blockage of the filter.

The effect of freezing/thawing was reflected in the final nanofiltration through 20 nm, both with respect to the maximum quantity of filterable fibrinogen, which could be much higher than 30.1 as opposed to 23.7 g/m², and with respect to the filtration flow rate of 21.20 as opposed to 4.74 g of fibrinogen/m²/hour, which is 4.5 times higher. The area of nanofiltration through 20 nm. can obviously be reduced by the same proportion, and this allows optimisation of the high costs of nanofiltration which, in practice, would prevent the industrial introduction thereof for this type of high molecular weight protein.

Example 4

As a result of the foregoing example 3, the optimum conditions for achieving thawing of the product were sought with the aim of removing the majority of the insoluble or insolubilisable material formed principally by aggregates, and minimising the losses of monodisperse fibrinogen.

Various batches, processed as in example 1 to the solution frozen at −70° C., were thawed under controlled conditions (temperature and melting time). Once the material had thawed, the insoluble material was separated. Said material was separated through a nylon mesh having a pore size of 20 microns and at the temperature at which the frozen material thawed. Once the insoluble material had been separated, the solution was heated to 30° C. and filtered through 0.45 microns (Millipore's CHVL filter).

The weight of separated insoluble material as well as the protein concentration (approximate, through optical density at 280 nm) of the solution were determined.

The values obtained are shown in Table 3.

TABLE 3

| Process | Thawing temperature (° C.) | Weight of insoluble material (kg) | OD (280) prior to freezing (AU) | OD (280) after freezing and filtration (AU) | Difference in OD (AU) | % Protein recovery |
|---|---|---|---|---|---|---|
| 1 | 5-10 | 2.0 | ND | ND | NA | NA |
| 2 | 30.5 | 0.1 | 47.8 | 46.5 | 1.3 | 97.5 |
| 3 | 9 ± 1 | 1.0 | 45.2 | 37.5 | 7.7 | 83.0 |
| 4 | 19 ± 1 | 0.5 | 39.5 | 34.3 | 5.2 | 86.8 |
| 5 | 7 ± 1 | 1.9 | 35.0 | 24.5 | 10.5 | 70.0 |
| 6 | 11 ± 2 | 0.9 | 36.0 | 31.5 | 4.5 | 87.5 |

The foregoing results show clearly that the quantity of insoluble residue formed is related to the thawing temperature and corresponds to the decrease in protein concentration (optical density) of the filtrate with respect to the initial solution before freezing. Similarly, the melting temperature of around 10° C. is adequate to recover sufficient protein and remove the insoluble material. 0.5 to 1.0 kg of insoluble material separates between 9 and 19° C. and 83% to 87% of protein are recovered. It is significant that hardly any precipitate is obtained at 30.5° C. (0.1 kg) and an appropriate reduction in the protein present is not detected.

Example 5

The effect of the various thawing conditions from example 4 on the filterability of the product during nanofiltration is shown in table 4.

The processed batches, thawed and filtered as mentioned in example 4, were diluted to an optical density (280 nm) of 1.2 to 1.3 AU (approximately 0.8 mg/ml of fibrinogen) with a 2% (w/v) arginine solution which contained sodium chloride/citrate, at pH 7.0 and a temperature of 30° C. Nanofiltration was carried out in two stages through 0.1 microns (30" CVVL) and 50 nm (2×30" DV50) and then through 20 nm (3×30" DV20) at a pressure of 2.2 to 2.8 bar in each stage.

The filtration capacity (g of fibrinogen/m$^2$, filtered), the volume filtered, the recovery of fibrinogen (by optical density at 280 nm) and the filtration time were determined in each process. The results are shown in Table 4.

TABLE 4

| Process | Thawing temperature (° C.) | Production capacity (kg solution/m$^2$) | Filtration time (h) | Filtration flow rate (kg/m$^2$/h) |
|---|---|---|---|---|
| 1 | 5-10 | >43.8 | 3.0 | 14.6 |
| 3 | 9 ± 1 | >56.3 | 6.5 | 8.7 |
| 4 | 19 ± 1 | >51.7 | 8.5 | 6.1 |
| 5 | 7 ± 1 | >27.1 | 3.0 | 9.0 |
| 6 | 11 ± 2 | >32.8 | 3.8 | 8.6 |

It follows from the values obtained that it is possible to nanofilter fibrinogen through 20 nm on an industrial scale. Similarly, the filtration times (or rather the flow rates may be correlated with the thawing temperature of the starting material from example 4, demonstrating that, in practice, temperatures below 20° C., preferably between 7 and 19° C., will be the most convenient for nanofiltration through 20 nm with a reasonable production capacity and processing time and without excessive reductions in product due to losses during thawing.

It is therefore found that, by applying the present invention, it is possible to purify plasma fibrinogen solutions by nanofiltration using filters having a nominal pore size smaller than 35 nm under conditions which allow the industrial application thereof to the production of purified fibrinogen as a therapeutic product.

Although the present invention has been described through the content of the description and the accompanying examples, it will be appreciated that it is not strictly limited to the substance of said description and examples, which basically have a non-limiting illustrative character and that experts in this field, on the basis of the material disclosed in the present description and examples, will be able to make modifications and variations which will be fully included in the scope of the present invention, as defined in the present claims.

The invention claimed is:

1. A process for removing viruses in fibrinogen solutions for therapeutic application, comprising:
    (a) obtaining a fibrinogen solution originating from previously purified human plasma, with a purity greater than or equal to 80% of fibrinogen with respect to the total proteins;
    (b) stabilizing and freezing said fibrinogen solution and subsequent thawing thereof at a temperature between 5 and 20° C.;
    (c) separating the undissolved materials;
    (d) diluting the resultant protein solution; and
    (e) nanofiltration of the diluted solution through a filter having a pore size smaller than 35 nm;
    wherein the freezing, thawing and nanofiltration are carried out in the presence of at least one amino acid.

2. The process for removing viruses in. fibrinogen solutions for therapeutic application according to claim 1, wherein the amino acid is arginine or glycine or combinations of the two.

3. The process for removing viruses in fibrinogen solutions for therapeutic application according to claim 1, wherein the undissolved material is separated by a mesh filter after freezing and thawing.

4. The process for removing viruses in fibrinogen solutions. for therapeutic application according to claim 1, wherein the undissolved material is separated by decanting after freezing and thawing.

5. The process for removing viruses in fibrinogen solutions for therapeutic application according to claim 1, wherein the undissolved material is separated. by centrifuging after freezing and thawing, 6. The process for removing viruses in fibrinogen solutions for therapeutic application according to claim 1, wherein the undissolved material is separated by direct filtration or by a gradient of filters after freezing and thawing.

7. The process for removing viruses in fibrinogen solutions for therapeutic application according to claim 1, wherein the undissolved material is separated by a mesh filter, decanting, centrifuging, direct filtration, a gradient of filters, or combinations thereof, after freezing and thawing.

8. The process for removing viruses in fibrinogen solutions for therapeutic application according to claim 1, wherein said resultant protein solution is diluted to a concentration less than or equal to 1.5 mg/ml of fibrinogen.

9. The process for removing viruses in fibrinogen solutions for therapeutic application according to claim 1, wherein said diluted solution is adjusted to a temperature between 18 and 37° C. prior to nanofiltration.

10. The process for removing viruses in fibrinogen solutions for therapeutic application according to claim 1, wherein said diluted solution is pre-filtered through filters having a pore size greater than or equal to 35 nm prior to nanofiltration.

11. The process for removing viruses in fibrinogen solutions for therapeutic application according to claim 1, wherein the filter area for nanofiltration through a filter having a pore size smaller than 35 nm is between 10 and 1,000 $cm^2$ per liter of solution to be filtered.

12. The process for removing viruses in fibrinogen solutions for therapeutic application according to claim 1, wherein the thawing temperature is between 8 and 13° C.

13. The process for removing viruses in fibrinogen solutions for therapeutic application according to claim 1, wherein the amino acid concentration is greater than 0.1%.

14. The process for removing viruses in fibrinogen solutions for therapeutic application according to claim 13, wherein the amino acid concentration is between 0.1 and 8%.

15. The process of claim 1, wherein the filter has a pore size of 20 run or smaller.

16. A process for removing viruses in fibrinogen solutions for therapeutic application, comprising:
(a) obtaining a fibrinogen solution originating from previously purified human plasma, with a purity greater than or equal to 80% of fibrinogen with respect to the total proteins;
(b) stabilizing and freezing said fibrinogen solution and subsequent thawing thereof at a temperature between 5 and 20° C.;
(c) separating the undissolved materials;
(d) obtaining an arginine solution;
(e) diluting the resultant protein solution with the arginine solution;
(f) nanofiltering the diluted solution through a first filter having a pore size of 50 nm; and
(g) nanofiltering the diluted solution through a second filter having a pore size of 20 nm.

* * * * *